United States Patent [19]

Magee, Jr.

[11] 4,351,775

[45] Sep. 28, 1982

[54] METHOD FOR PREPARATION OF ALKYL VANADATES

[75] Inventor: Walter L. Magee, Jr., Danbury, Conn.

[73] Assignee: Stauffer Chemical Company, Westport, Conn.

[21] Appl. No.: 245,868

[22] Filed: Mar. 20, 1981

[51] Int. Cl.$^3$ .............................................. C07F 9/00
[52] U.S. Cl. .............................................. 260/429 R
[58] Field of Search .................................. 260/429 R

[56] References Cited

U.S. PATENT DOCUMENTS

| | | | |
|---|---|---|---|
| 3,657,295 | 4/1972 | McCoy | 260/429 R |
| 3,920,713 | 11/1975 | Feichtinger et al. | 260/429 R |
| 3,920,751 | 11/1975 | Chabardes et al. | 260/429 R |
| 3,987,074 | 10/1976 | Haase et al. | 260/429 R |
| 4,014,911 | 3/1977 | Muntz et al. | 260/429 R |
| 4,014,912 | 3/1977 | Muntz et al. | 260/429 R |

*Primary Examiner*—Helen M. S. Sneed
*Attorney, Agent, or Firm*—Richard P. Fennelly

[57] ABSTRACT

Alkyl vanadates are prepared by the reaction of vanadium pentoxide and an alkyl alcohol while heating in the presence of an alkane azeotroping agent to assist in the removal of water by-product.

7 Claims, No Drawings

METHOD FOR PREPARATION OF ALKYL VANADATES

BACKGROUND OF THE INVENTION

1. Field of the Invention

The present invention is a process for forming alkyl vanadates by the reaction of vanadium pentoxide and an alkyl alcohol.

2. Description of the Prior Art

The preparation of alkyl vanadates, which are useful as catalysts, by means of the reaction of vanadium pentoxide and an alkyl alcohol has been characterized as one which involves "great difficulty" (U.S. Pat. No. 3,987,074 to R. Haase at Col. 1, lines 28–29) in regard to removing by-product water to drive the reaction to a greater degree of completion. A number of techniques to remove by-product water have been proposed including the use of certain specific azeotroping solvents as the reaction medium. For example, in Bull. Acad. Sci. U.S.S.R. 1959, pp. 899–900 and in U.S. Pat. No. 3,920,751 to P. Charbardes et al. (Examples 5 and 6), the specific use of benzene as an azeotroping solvent is proposed. An improvement to this technique in which toluene, a specific aromatic solvent, is suggested, is described in U.S. Pat. No. 3,657,295 to D. R. McCoy. The patent to McCoy also shows that use of xylene, another aromatic solvent, is ineffective.

SUMMARY OF THE PRESENT INVENTION

The present invention is a process for forming alkyl vanadates by the reaction of vanadium pentoxide and an alkyl alcohol while heating these reactants in an alkane azeotroping solvent to assist in the removal of water by-product.

DESCRIPTION OF PREFERRED EMBODIMENTS OF THE INVENTION

The reactants that are used in practicing the present invention are vanadium pentoxide and an alkyl alcohol. The selection of the alkyl alcohol will depend upon the alkyl group desired in the alkyl vanadate product. Use of alkyl alcohols containing any of the $C_2$ to $C_6$ straight or branched alkyl groups is contemplated in accordance with the present invention. Branched chain alcohols are generally preferred, since they yield a vanadate product having improved thermal stability. Representative examples of such alkyl alcohols include ethanol, butanol, isobutanol, amyl alcohol, and isoamyl alcohol. Generally, the use of an excess amount of alcohol is preferred since it tends to increase the rate of reaction.

The present invention contemplates the use of an alkane solvent to serve as an azeotroping agent when the reaction is run under reflux conditions. In selecting the particular alkane azeotroping agent, one should select one which insures that by-product water from the reaction will preferentially co-distill with the alkane at a high concentration of water. The boiling point of the alcohol should also be high enough to ensure that it is present to assist in the removal of the water when the reaction is taking place. Its boiling point should not be so high as to decompose the desired vanadate product or to require the input of excessive amounts of heat energy to initiate and sustain the desired reaction. It is also preferred, in certain embodiments, that the alkane solvent be less dense than water to produce water as the overhead phase in the separation apparatus to assist in its removal. Those alkane solvents that can be used include those liquid, straight and branched chain alkanes and cycloalkanes having a boiling point, for example, in the range of from about 90° C. to about 130° C. Representative alkane solvents of this type include hexane, heptane, octane, isooctane, and cyclohexane.

The reaction is conducted by admixing the desired quantities, as described below, of vanadium, pentoxide, alkyl alcohol, and alkane solvent in a reaction vessel and refluxing the contents of the reactor while maintaining an inert gas blanket over the reaction mixture. During the refluxing operation, the condensed liquid is passed through a trap where a hydrocarbon rich layer will form. Drawing off the water rich layer will remove at least a portion of the water of formation while the remaining liquid (a mixture of alcohol and alkane) is returned to the reactor.

Generally, the process can be practiced with a mole ratio of alkyl alcohol to vanadium pentoxide of from about 3:1 to about 12:1. The amount of alkane solvent to alcohol which can be used ranges from about 0.05:1 to about 3:1 on a weight basis.

The following Examples illustrate certain preferred embodiments of the present invention.

EXAMPLE 1

This Example illustrates a bench scale synthesis in accordance with the present invention.

Vanadium pentoxide (182 gm.) was charged into a two liter, three neck vessel equipped with thermometer, a 4 in. mechanical stirrer operated at 200 rpm. and Dean-Stark trap condenser. The vessel also contained a mixture of isobutyl alcohol (444 gm.) and n-heptane (650 gm.). The resulting mixture was heated to reflux under nitrogen. The condensed overhead phase was sent to a phase separator where water was removed, and the organic phase was returned to the reactor. During the first six hours of reflux, about 20 ml. of water was removed. During the next three hours only 3 ml. of water was collected. The reaction was terminated by cooling, and the mixture was allowed to settle. Filtration produced 1518 gm. of liquid and a 116 gm. filter cake. The filter cake was washed with 170 gm. of n-heptane. The liquid phase containing solvents and the desired product was decanted and transferred to a vessel equipped for vacuum distillation. The solvents were stripped at 80°–90° C. with the pressure being gradually reduced to 10–20 mm. Hg until no volatiles were collected. The amount of isobutanol and n-heptane that was recovered totalled 918 gm. The triisobutyl vanadate product weighed 250 gm. or 44% of theoretical, based on the weight of isolated product with $V_2O_5$ as the limiting reactant.

EXAMPLE 2

This Example illustrates the preparation of triisobutyl vanadate by the reaction of isobutanol and vanadium pentoxide in the presence of an n-heptane azeotroping solvent.

Vacuum was applied to a 380 liter pilot plant reactor, and the vacuum was released with nitrogen. Vacuum was applied again, and the reactor was charged with 107 kg. of isobutanol and 159 kg. of n-heptane. The vacuum was released using nitrogen, and the agitator in the reactor was turned on. To the reactor was then added 35 kg. of vanadium pentoxide. Heating was initiated, and refluxing began at about 90° C. Refluxing was continued, and water by-product formed by the reaction was entrained by the solvents and was periodically removed through a trap. The reaction was allowed to run for approximately 18 hours at a temperature of 90° to 94° C. at the end of which time about 2.3 kg. of water of reaction was collected. The reactor was then allowed to cool to about 30° C. The resulting mixture was filtered to yield a filter cake of unreacted $V_2O_5$ having a weight of about 34.5 kg. This filter cake was washed with n-heptane and dried.

The filtrate containing a mixture of n-heptane, isobutanol, and triisobutyl vanadate product was added to a second reactor and was heated to about 94° C. under application of no vacuum (760 mm Hg.). The solvent was removed, and distillation was continued at about 77° C. and a pressure of 14 mm Hg. to complete removal of the remaining solvent. This reactor was then cooled and the triisobutyl vanadate product (28 kg.) was removed. The yield of the product was 25% of theoretical, using the same basis as Example 1.

EXAMPLE 3

This Example illustrates the preparation of triisobutyl vanadate by the reaction of isobutanol and vanadium pentoxide in the presence of an n-heptane azeotroping solvent.

Vacuum was applied to a 1920 liter pilot plant reactor, and the vacuum was released with nitrogen. Vacuum was applied again, and the reactor was charged with 493 kg. of isobutanol and 681 kg. of n-heptane. The vacuum was released using nitrogen, and the agitator in the reactor was turned on. To the reactor was then added 142 kg. of vanadium pentoxide. Heating was initiated, and refluxing began at about 85° C. Refluxing was continued, and water by-product formed by the reaction was entrained by the solvents and was periodically removed through a trap. The reaction was allowed to run for approximately 42 hours at a temperature of 85° to 93° C. at the end of which time about 17 kg. of water of reaction was collected. The reactor was then allowed to cool to about 30° C. The resulting mixture was filtered to yield a filter cake of unreacted $V_2O_5$ having a weight of about 136 kg. This filter cake was washed with n-heptane and dried.

The filtrate containing a mixture of n-heptane, isobutanol, and triisobutyl vanadate product was added to a second reactor and was heated to about 25° C. under application of slight vacuum (600 mm Kg.). The solvent was removed, and distillation was continued at about 90° C. and a pressure of 15 mm Hg. to complete removal of the remaining solvent. This reactor was then cooled and the triisobutyl vanadate product (155 kg.) was removed. The yield of the product was 35% of theoretical, using the same basis as Example 1.

EXAMPLE 4

This Example illustrates the preparation of triisobutyl vanadate by the reaction of isobutanol and vanadium pentoxide in the presence of a n-heptane azeotroping solvent.

Vacuum was applied to a 1920 liter pilot plant reactor, and the vacuum was released with nitrogen. Vacuum was applied again, and the reactor was charged with 573 kg. of isobutanol and 857 kg. of n-heptane. The vacuum was released using nitrogen, and the agitator in the reactor was turned on. To the reactor was then added 181.5 kg. of vanadium pentoxide. Heating was initiated, and refluxing began at about 85° C. Refluxing was continued, and water by-product formed by the reaction was entrained by the solvents and was periodically removed through a trap. The reaction was allowed to run for approximately 41 hours at a temperature of 88° to 93° C. at the end of which time about 19.5 kg. of water or reaction was collected. The reactor was then allowed to cool to about 30° C. The resulting mixture was filtered to a yield a filter cake of unreacted $V_2O_5$ having a weight of about 194 kg. This filter cake was washed with n-heptane and dried.

The filtrate containing a mixture of n-heptane, isobutanol, and triisobutyl vanadate product was added to a second reactor and was heated to about 85° C. under application of slight vacuum (600 mm Hg.). The solvent was removed, and distillation was continued at about 85° C. and a pressure of 14 mm Hg. to complete removal of the remaining solvent. This reactor was then cooled and the triisobutyl vanadate product (116 kg.) was removed. The yield of the product was 20% of theoretical, using the same basis as Example 1.

EXAMPLE 5

This Example illustrates the preparation of triisobutyl vanadate by the reaction of isobutanol and vanadium pentoxide in the presence of an n-heptane azeotroping solvent.

Vacuum was applied to a 1920 liter pilot plant reactor, and the vacuum was released with nitrogen. Vacuum was applied again, and the reactor was charged with 336 kg. of isobutanol and 556 kg. of n-heptane. The vacuum was released using nitrogen, and the agitator in the reactor was turned on. To the reactor was then added 136 kg. of vanadium pentoxide. Heating was initiated, and refluxing began at about 85° C. Refluxing was continued, and water by-product formed by the reaction was entrained by the solvents and was periodically removed through a trap. The reaction was allowed to run for approximately 24 hours at a temperature of 90° to 93° C. at the end of which time about 12 kg. of water of reaction was collected. The reactor was then allowed to cool to about 30° C. The resulting mixture was filtered to yield a filter cake of unreacted $V_2O_5$. This filter cake was washed with n-heptane and dried.

The filtrate containing a mixture of n-heptane, isobutanol, and triisobutyl vanadate product was added to a second reactor and was heated to about 75° C. under application of slight vacuum (500 mm Hg.). The solvent was removed, and distillation was continued at about 90° C. and a pressure of 20 mm Hg. to complete removal of the remaining solvent. This reactor was then cooled and the triisobutyl vanadate product (77 kg.) was removed. The yield of the product was 18% of theoretical, using the same basis as Example 1.

EXAMPLE 6

Vanadium pentoxide (376 gm.), isobutyl alcohol (800 gm.) and heptane (100 ml.) were added to a 1000 ml. reactor equipped with heating mantle, Heller mixer, Dean-Stark trap condenser, thermometer and vacuum pump. The mixture was heated and allowed to reflux. The Table given below shows the time of reaction from the beginning of reflux, the amount of by-product water collected as the reaction proceeded during formation of triisobutyl vanadate, and the temperature of the reaction:

| Time (hrs.:min.) | Temp. (°C.) | ml.H₂O |
|---|---|---|
| 0:00 | 96 | — |
| 0:15 | 98 | 2.5 |
| 0:30 | 100 | 11.0 |
| 0:45 | 101 | 14.0 |
| 1:00 | 101 | 17.5 |
| 1:25 | 102 | 20.1 |
| 1:45 | 102.5 | 23.5 |
| 2:15 | 103 | 25.0 |
| 2:30 | 103 | 27.0 |
| 3:15 | 104 | 30.0 |
| 4:30 | 104.5 | 33.5 |

The yield of product was 33% of the theoretical yield, based on the amount of by-product water evolved using $V_2O_5$ as the limiting reactant.

EXAMPLE 7

Vanadium pentoxide (375 gm.), isobutyl alcohol (800 gm.), and heptane (100 ml.) were added to a 2 liter round bottom flask equipped with Dean-Stark trap, Heller mixer, thermometer and heating mantle, and the reaction mixture was heated to initiate the reaction. After approximately 8-½ hours of reaction a total of 42 ml. of water by-product was collected. The percentage yield was 39% of theoretical, using the same basis as in Example 6.

EXAMPLE 8

The same procedure used in Example 7 was employed with 1125 gm. of vanadium pentoxide, 2400 gm. of isobutyl alcohol, and 300 gm. of heptane. After approximately 10-¼ hours of reaction, a total of about 94 ml. of by-product water was recovered. The percentage yield was 30% of theoretical, using the same basis as in Example 6.

EXAMPLE 9

This illustrates the results obtained using the process of the present invention (Run A) and a toluene azeotroping agent, as shown in U.S. Pat. No. 3,657,295 to D. R. McCoy (Run B).

Isobutyl alcohol (222 gm.), vanadium pentoxide (91 gm.) and either heptane or toluene (475 ml.) were charged into a 1000 ml. three neck flask equipped with thermometer, mechanical stirrer, Dean Stark trap condenser and heating mantle. The flask was heated and brought to reflux so that by-product water was removed in the trap. The Table set forth below gives the time of reaction (in minutes) and the amount of water collected:

| Reaction Time | H₂O Collected (ml.) Run A* | Run B |
|---|---|---|
| 30 | 0.5 | 0.5 |
| 40 | 3.0 | 4.0 |
| 50 | 5.5 | 6.1 |
| 60 | 6.3 | 7.2 |
| 70 | 7.1 | 8.0 |
| 90 | 8.3 | 9.0 |
| 120 | 9.5 | 10.0 |
| 180 | 10.5 | 11.0 |
| 240 | 11.5 | 11.5 |
| 300 | 12.0 | 12.0 |
| 360 | 12.5 | 12.2 |
| 480 | 13.0 | 12.5 |

*process of the present invention.

The reaction mixture was allowed to cool and was filtered under a nitrogen tent through a CELITE brand filter. The respective filter cakes were washed with an appropriate solvent (Run A: 254 gm. of heptane and Run B: 201 gm. of toluene). Refiltration removed some observed cloudiness in each filtrate.

The filtrates were transferred to 2-liter flasks and each was stripped for 2–4 hours at atmospheric pressure to 10–20 mm Hg. with the pressure gradually being reduced during the stripping operation to avoid bumping or foaming.

The yield of materials for each run was as follows:

| Material | Run A* | Run B |
|---|---|---|
| Triisobutyl vanadate | 106.1 gm. | 126.8 gm. |
| Volatiles | 510.7 gm. | 617.5 gm. |
| Water | 13.0 gm. | 12.5 gm. |
| Sludge | 75.3 gm. | 82.2 gm. |

*process of this invention.

The percent yield of triisobutyl vanadate in Run A was 39% of theoretical, using the same basis as in Example 1.

The foregoing Examples should not be construed in a limiting sense. The scope of protection that is sought is set forth in the claims which follow.

What is claimed is:

1. A method of preparing an alkyl vanadate which comprises heating vanadium pentoxide and an alkyl alcohol in an alkane solvent to assist in the removal of by-product water.

2. A method as claimed in claim 1 wherein the alkyl alcohol is one having a boiling point in the range of from about 90° C. to about 130° C.

3. A method as claimed in claim 1 wherein the alkyl alcohol is selected from the group consisting of hexane, heptane, octane, isooctane and cyclohexane.

4. A method as claimed in either claim 1, 2 or 3 wherein the alkane is heptane.

5. A method as claimed in either claim 1, 2 or 3 wherein the molar ratio of alkyl alcohol to vanadium pentoxide ranges from about 3:1 to about 12:1.

6. A method as claimed in either claim 1, 2, or 3 wherein the amount of alkane to alcohol ranges from about 0.05:1 to about 3:1 on a weight basis.

7. A method as claimed in either claim 1, 2 or 3 wherein the alkane is heptane and is present to alcohol at from about 0.05:1 to about 3:1 on a weight basis and the molar ratio of alcohol to vanadium pentoxide ranges from about 3:1 to about 12:1.

* * * * *